US00PP12044P2

(12) United States Plant Patent
Gross

(10) Patent No.: US PP12,044 P2
(45) Date of Patent: Aug. 7, 2001

(54) POINSETTIA PLANT NAMED 'SOLE MIO'

(75) Inventor: Eduard Gross, Blanzac (FR)

(73) Assignee: Paul Ecke Ranch, Inc., Encinitas, CA (US)

( * ) Notice: Subject to any disclaimer, the term of this patent is extended or adjusted under 35 U.S.C. 154(b) by 0 days.

(21) Appl. No.: 09/563,750

(22) Filed: May 4, 2000

(51) Int. Cl.[7] ..... A01H 5/00
(52) U.S. Cl. ..... Plt./307

(58) Field of Search ..... Plt./303, 306, 307

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Poinsettia plant named 'Sole Mio', characterized by its dark orange red-colored flower bracts; red-colored nectaries; dark green leaves; compact, upright and outwardly spreading plant habit; very freely branching habit; early flowering; and excellent post-production longevity.

2 Drawing Sheets

BACKGROUND OF THE INVENTION

The present Invention relates to a new and distinct cultivar of Poinsettia plant, botanically known as *Euphorbia pulcherrima* Willd., and hereinafter referred to by name 'Sole Mio'. The new Poinsettia is a naturally-occurring whole plant mutation of the *Euphorbia pulcherrima* Willd. cultivar 'EDA Pink', not patented. The new Poinsettia was discovered and selected by the Inventor in a controlled environment in Blanzac, France. Compared to plants of the parent cultivar, plants of the new Poinsettia are shorter, have smaller leaves and differ in flower bract color.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Sole Mio'. These characteristics in combination distinguish 'Sole Mio' as a new and distinct cultivar:

1. Dark orange red-colored flower bracts.
2. Red-colored nectaries.
3. Dark green leaves.
4. Compact, upright and outwardly spreading plant habit.
5. Very freely branching habit.
6. Early flowering.
7. Excellent post-production longevity.

Plants of the new Poinsettia can be compared to plants of the Poinsettia cultivar 'Peterstar', disclosed in U.S. Plant Pat. No. 8,259. In side-by-side comparisons conducted in Encinitas, Calif., plants of the new Poinsettia differed from plants of the cultivar 'Peterstar' in the following characteristics:

1. Plants of the new Poinsettia are slightly shorter, but more outwardly spreading than plants of the cultivar 'Peterstar'.
2. Plants of the new Poinsettia have slightly smaller leaves and slightly shorter petioles than plants of the cultivar 'Peterstar'.

3. Plants of the new Poinsettia have smaller but more pointed flower bracts than plants of the cultivar 'Peterstar'.
4. Plants of the new Poinsettia have smaller cyathia clusters than plants of the cultivar 'Peterstar'.
5. Flower bract color of the new Poinsettia is more orange than flower bract color of the cultivar 'Peterstar'.
6. Plants of the new Poinsettia have red-colored nectaries whereas plants of the cultivar 'Peterstar' have yellow-colored nectaries.
7. Plants of the new Poinsettia have longer post-production longevity than plants of the cultivar 'Peterstar'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the actual colors of the new Poinsettia.

The photograph at the top of the first sheet comprises a side perspective view of a typical plant of 'Sole Mio'.

The photograph at the bottom of the first sheet comprises a top perspective view of a typical plant of 'Sole Mio'.

The photograph at the top of the second sheet is a close-up view of a typical inflorescence of 'Sole Mio'.

The photograph at the bottom of the second sheet is a close-up view of typical bracts and leaves of 'Sole Mio' (left) and 'Peterstar' (right).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following obseravtions and measurements describe plants grown in Encinitas, Calif., under commercial practice in a glass-covered greenhouse with day temperatures about 21 to 27° C., night temperatures about 18 to 20° C., and light levels about 4,000 foot-candles. Plants were grown in 16.5-cm pots, pinched one time, and flowered under naturally lengthening nyctoperiods during the fall. Plants described were about 17 weeks old.

In the following description, color references are made to The Royal Horticultural Society Colour Chart except where general terms of ordinary dictionary significance are used.

Botanical classification: *Euphorbia pulcherrima* Willd. cultivar 'Sole Mio'.

Parentage: Naturally-occuring whole plant mutation of *Euphorbia pulcherrima* Willd. cultivar 'EDA Pink', not patented.

Propagation:

*Type cutting.*—Terminal cuttings.

*Time to initiate roots.*—Summer: About 7 days at 24° C. Winter: About 10 days at 22° C.

*Time to develop roots.*—Summer: About 26 days at 24° C. Winter: About 26 days at 22° C.

*Root description.*—Thick, freely branching.

Plant description:

*Plant form.*—Inverted triangle, top of plant rounded; mounding.

*Growth habit.*—Compact, upright and outwardly spreading. Very freely branching. Branching is enhanced by removing the shoot apex. Moderately vigorous to vigorous.

*Plant height.*—About 25.5 cm.

*Crop time.*—From unrooted cuttings to a flowering plant in a 16.5-cm container, about 17 weeks are required.

*Stem description.*—Number of lateral branches: About 8 lateral branches develop after removal of the terminal apex. Lateral branch length: About 16.5 cm. Internode length: About 1.25 cm. Stem color: 146A; distally, occasional anthocyanin, 46B.

*Foliage description.*—Quantity of leaves per lateral branch: About 9. Length: About 10.25 cm. Width: About 5.25 cm. Shape: Mostly ovate. Apex: Acuminate. Base: Acute. Margin: Entire. Texture: Smooth; very slight pubescence on lower surface. Color: Young foliage, upper surface: 146A. Young foliage, lower surface: 146B. Mature foliage, upper surface: 147A. Mature foliage, lower surface: 147B. Venation, upper surface: 144A. Venation, lower surface: 147C. Petiole: Length: About 3.75 cm. Diameter: About 2 mm. Color: 60A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions. Early flowering, response time is about 8.5 weeks.

*Quantity of inflorescences.*—One per lateral branch, usually about 8 per plant.

*Inflorescence size.*—Diameter: About 30 cm. Height (depth): About 5 cm.

*Flower bracts.*—Quantity of flower bracts per inflorescence: Usually about 17 primary bracts and about 6 smaller secondary bracts per inflorescence. Length, largest bracts: About 16 cm. Width, largest bracts: About 8 cm. Shape: Mostly ovate. Apex: Acuminate. Base: Acute. Margin: Entire. Texture: Smooth. Aspect: Mostly flat. Color: Developing, upper surface: 44A. Developing, lower surface: 44C. Mature, upper surface: 43A; color does not fade with subsequent development. Mature, lower surface: 43B.

*Cyathia.*—Quantity: Usually about 15 per corymb. Diameter of cyathia cluster: About 2.5 cm. Length: About 9 mm. Width: About 5 mm. Color: Immature: 144B. Mature: 144A.

*Peduncle.*—Length: About 4 mm. Aspect: Strong, erect. Color: 144B.

*Reproductive organs.*—Stamens: Stamen number: Typically more than 20 per cyathium. Anther shape: Oblong. Anther length: About 1 mm. Anther color: 45A. Amount of pollen: Scarce. Pollen color: 8B. Pistils: Quantity: One. Length: About 9 mm. Stigma shape: Tri-lobate. Stigma color: 46A. Style color: 46B. Nectary color: Immature: 46A. Mature: 28A.

Disease resistance: Resistance to pathogens common to Poinsettias has not been observed on plants grown under commercial conditions.

Post production longevity: Generally plants maintain good substance and bract color for about six weeks under interior conditions.

It is claimed:

1. A new and distinct cultivar of Poinsettia plant named 'Sole Mio', as illustrated and described.

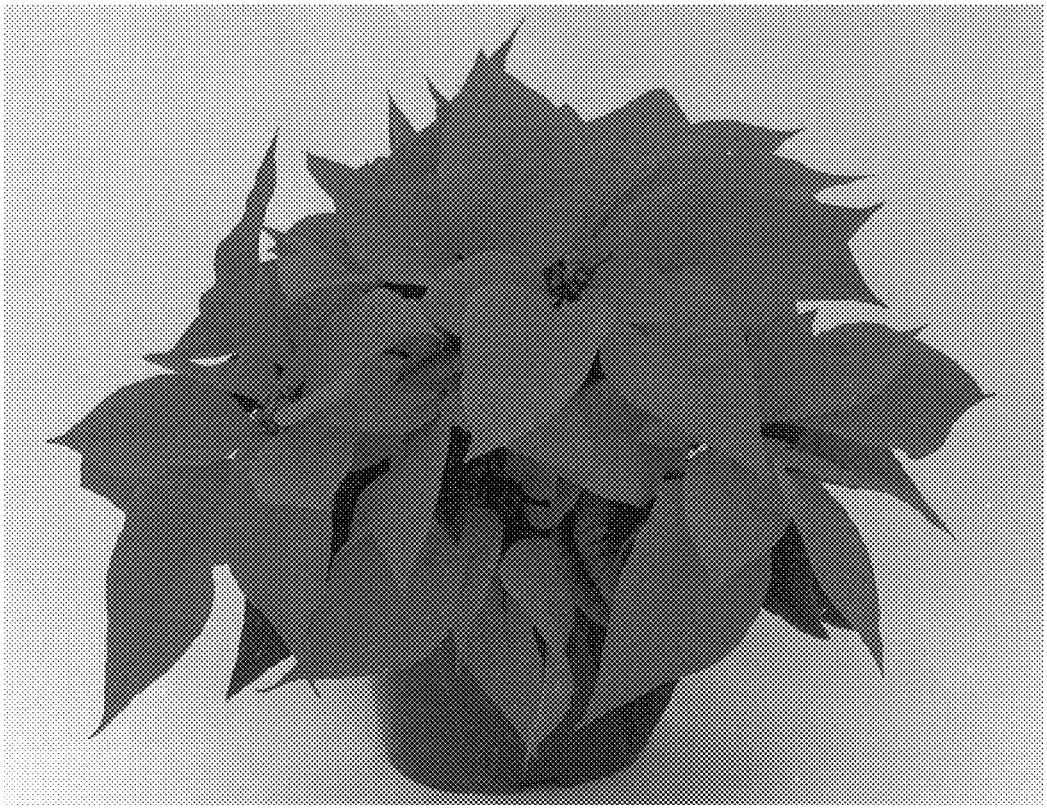
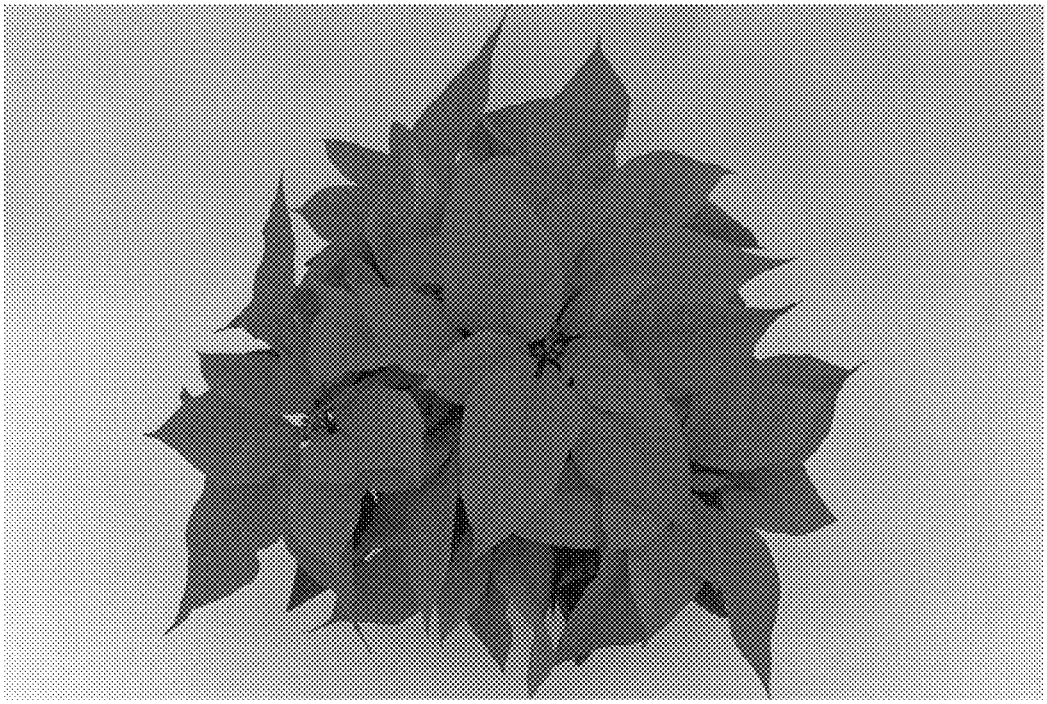

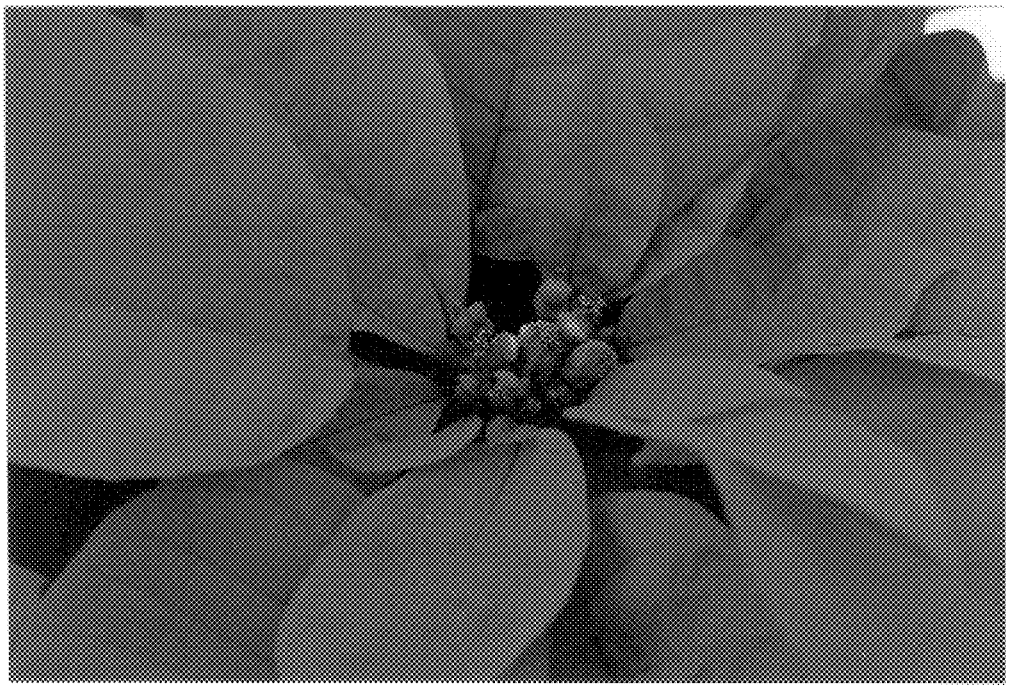
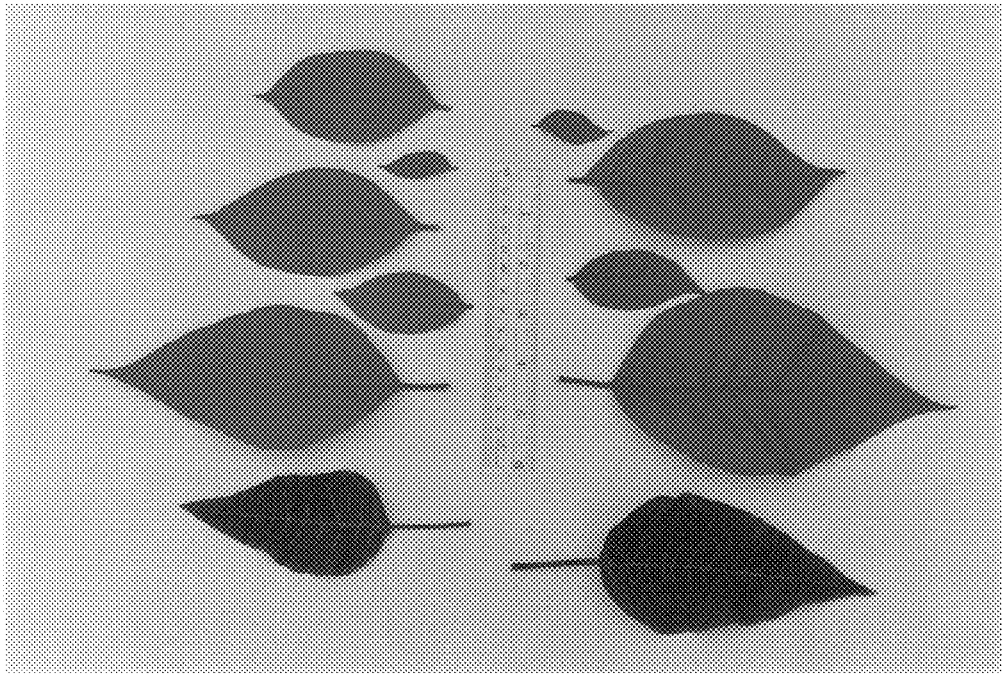

* * * * *